United States Patent
Greving et al.

(10) Patent No.: US 7,865,315 B2
(45) Date of Patent: Jan. 4, 2011

(54) METHODS AND APPARATUS FOR CALIBRATING STRIATION DENSITY MODELS FOR MATERIALS

(75) Inventors: Daniel J. Greving, Scottsdale, AZ (US); Chris Desadier, Conroe, TX (US)

(73) Assignee: Honeywell International Inc., Morristown, NJ (US)

( * ) Notice: Subject to any disclaimer, the term of this patent is extended or adjusted under 35 U.S.C. 154(b) by 457 days.

(21) Appl. No.: 11/942,915

(22) Filed: Nov. 20, 2007

(65) Prior Publication Data

US 2009/0132193 A1 May 21, 2009

(51) Int. Cl.
*G06F 19/00* (2006.01)

(52) U.S. Cl. .................... 702/34; 73/799; 73/865.9; 702/189

(58) Field of Classification Search .......... 73/1.01, 73/1.88, 760, 786, 787, 788, 789, 799, 802, 73/865.8, 865.9, 866; 702/1, 33, 34, 35, 702/36, 85, 88, 127, 187, 189
See application file for complete search history.

(56) References Cited

U.S. PATENT DOCUMENTS

| | | | | |
|---|---|---|---|---|
| 3,362,217 A | * | 1/1968 | Rush et al. | 73/112.01 |
| 3,979,949 A | * | 9/1976 | Smith | 73/787 |
| 3,983,745 A | * | 10/1976 | Juusola | 73/789 |
| 4,003,246 A | * | 1/1977 | Cain | 73/799 |
| 4,402,227 A | * | 9/1983 | Hayashi et al. | 73/812 |
| 4,764,970 A | * | 8/1988 | Hayashi et al. | 382/149 |
| 4,975,855 A | * | 12/1990 | Miller et al. | 702/35 |
| 5,068,800 A | * | 11/1991 | Brook et al. | 702/36 |
| 5,159,563 A | * | 10/1992 | Miller et al. | 702/35 |
| 5,531,123 A | | 7/1996 | Henkel | |
| 5,789,680 A | | 8/1998 | Fujumoto | |
| 5,929,315 A | * | 7/1999 | Dunegan | 73/1.82 |
| 6,062,083 A | * | 5/2000 | Dunegan | 73/587 |
| 6,173,613 B1 | * | 1/2001 | Dunegan | 73/587 |

OTHER PUBLICATIONS

Au, J.J., et al., Correlation between fatigue crack growth rate and fatigue striation spacing in AISI9310 (AMS 6265) Steel, Fractography and materials Science, ASTM STP 733, American Society for Testing Materials, 1981, 202-221.

* cited by examiner

*Primary Examiner*—Edward R Cosimano
(74) *Attorney, Agent, or Firm*—Ingrassia Fisher & Lorenz, P.C.

(57) ABSTRACT

A method for generating a calibration for a striation density model with respect to a material includes the steps of generating a first relationship between a striation density and a depth of a crack in a specimen comprising the material, generating a second relationship between the striation density and the depth of the crack in the specimen, and calculating an adjustment, based on a comparison between the first relationship and the second relationship.

20 Claims, 4 Drawing Sheets

METHODS AND APPARATUS FOR CALIBRATING STRIATION DENSITY MODELS FOR MATERIALS

FIELD OF THE INVENTION

The present invention relates to striation density models, and, more particularly, to improved methods and systems for calibrating striation density models for materials.

BACKGROUND OF THE INVENTION

Striation density analysis is often performed on cracked components of devices to ascertain information regarding crack propagation and durability of the components. For example, with respect to gas turbine engines, striation density analysis is often performed on a component of the engine, such as a turbine blade, a turbine disk, or another component, to estimate an amount of operational stress the component has experienced and a number of operational cycles for which the component has operated before the component experienced a crack of a predetermined size. Such estimates can be used to predict the durability of similar components. For example, when a new component is used in an engine, it can then be removed or repaired before it has experienced the amount of operational stress and/or the number of operational cycles experienced by the analyzed component, or, in other words, before it is likely to have a crack of the predetermined size formed therein. In addition, striation density analysis can be used to ascertain similar information about various other devices, systems, and/or components thereof.

Striation density analysis typically involves use of a microscope, such as a scanning electronic microscope (SEM), in calculating a depth of a crack in a component, as well as counting a number of striations (which is often referred to as a striation density) at various locations along the crack. This information is then used, along with a striation density model, to generate a curve, function, and/or other model mapping striation density versus crack depth. This mapping of striation density versus crack depth is then used, along with standard fracture mechanics techniques, to estimate the amount of operational stress the component has experienced and the number of operational cycles for which the component has operated before the crack reached a predetermined size.

While striation density analysis techniques are valuable in ascertaining information regarding components and crack propagation, existing techniques are constrained by limitations in existing striation density models. For example, existing striation density models used to generate the mapping of striation density versus crack depth are not calibrated to specific materials, and therefore may not be of optimal accuracy, particularly during initial stages of crack propagation.

Accordingly, it is desirable to provide a method for generating a calibration for a striation density model with respect to a material of a component. In addition, it is desirable to provide a method for performing striation analysis for a component of an engine using a calibrated striation density model. It is also desirable to provide a program for performing striation analysis for a component of an engine using a calibrated striation density model. Furthermore, other desirable features and characteristics of the present invention will become apparent from the subsequent detailed description of the invention and the appended claims, taken in conjunction with the accompanying drawings and this background of the invention.

SUMMARY OF THE INVENTION

In accordance with an exemplary embodiment of the present invention, a method for generating a calibration for a striation density model with respect to a material is provided. The method comprises the steps of generating a first relationship between a striation density and a depth of a crack in a specimen comprising the material, generating a second relationship between the striation density and the depth of the crack in the specimen, and calculating an adjustment, based on a comparison between the first relationship and the second relationship.

In accordance with another exemplary embodiment of the present invention, a method for performing striation analysis for a component of an engine, the component comprising a material, is provided. The method comprises the steps of generating a first relationship between a striation density and a depth of a crack in the component, obtaining an adjustment, based at least in part on the material, and generating an adjusted relationship between the striation density and the depth of the crack in the component, based at least in part on the first relationship and the adjustment.

In accordance with a further exemplary embodiment of the present invention, a program product for performing striation analysis for a component of an engine, the component comprising a material, is provided. The program product comprises a program and a computer-readable signal bearing media. The program is configured to at least facilitate generating a first relationship between a striation density and a depth of a crack in the component, obtaining an adjustment to the relationship, based at least in part on the material, and generating an adjusted relationship between the striation density and the depth of the crack in the component, based at least in part on the first relationship and the adjustment. The computer-readable signal bearing media bears the program.

DETAILED DESCRIPTION OF A PREFERRED EMBODIMENT

Before proceeding with the detailed description, it is to be appreciated that the described embodiment is not limited to use in conjunction with a particular type of engine, or to engines in general. Thus, although the present embodiment is, for convenience of explanation, depicted and described as being implemented in connection with components of an engine, it will be appreciated that it can be implemented in connection with various other devices, systems, and/or environments.

Figure 1:
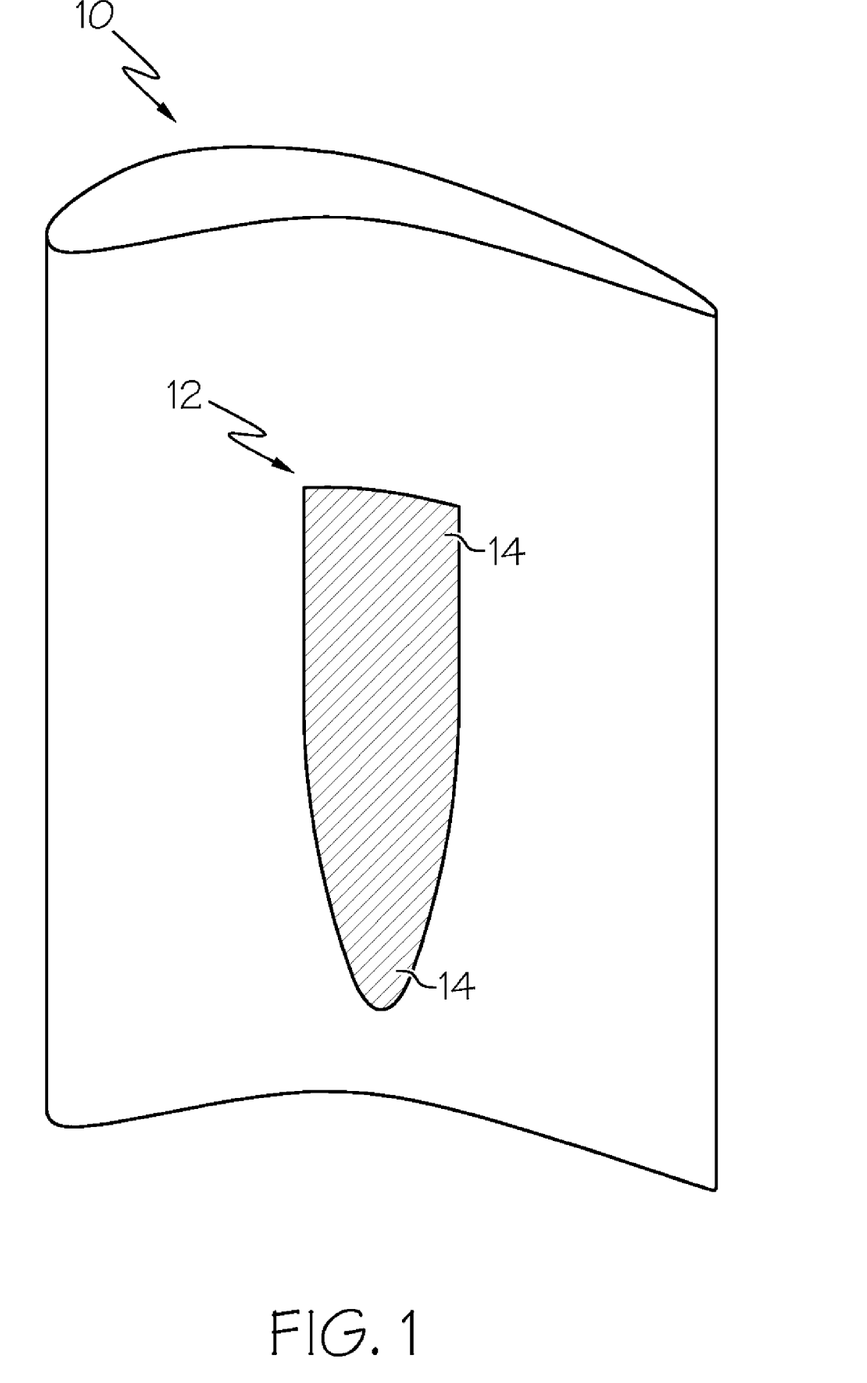
FIG. 1 is a side view of a turbine blade of a gas turbine engine, in accordance with an exemplary embodiment of the present invention.

FIG. 1 is a side view of a turbine blade 10 for a gas turbine engine, in accordance with an exemplary embodiment of the present invention. The turbine blade 10 comprises a material having a crack 12 formed therein. The crack has various striations 14 at different points along the crack 12, which can be related to a varying crack depth at such points along the crack 12. The number of striations 14 and the crack depth along the crack 12 can be analyzed to estimate a number of operational cycles and an amount of stress experienced by the turbine blade 10 before the crack 12 reached a predetermined size, to thereby predict a durability measure for the turbine blade 10 using a striation density analysis process. For example, when a new turbine blade similar to the turbine blade 10 (but without a crack) is used in an engine, it can be removed or repaired before it has experienced the amount of operational stress and/or the number of operational cycles estimated for the analyzed specimen, or, in other words, before it is likely to have a crack of the predetermined size formed therein. An exemplary embodiment of such a striation density analysis process will now be described below in connection with FIG. 2.

Figure 2:
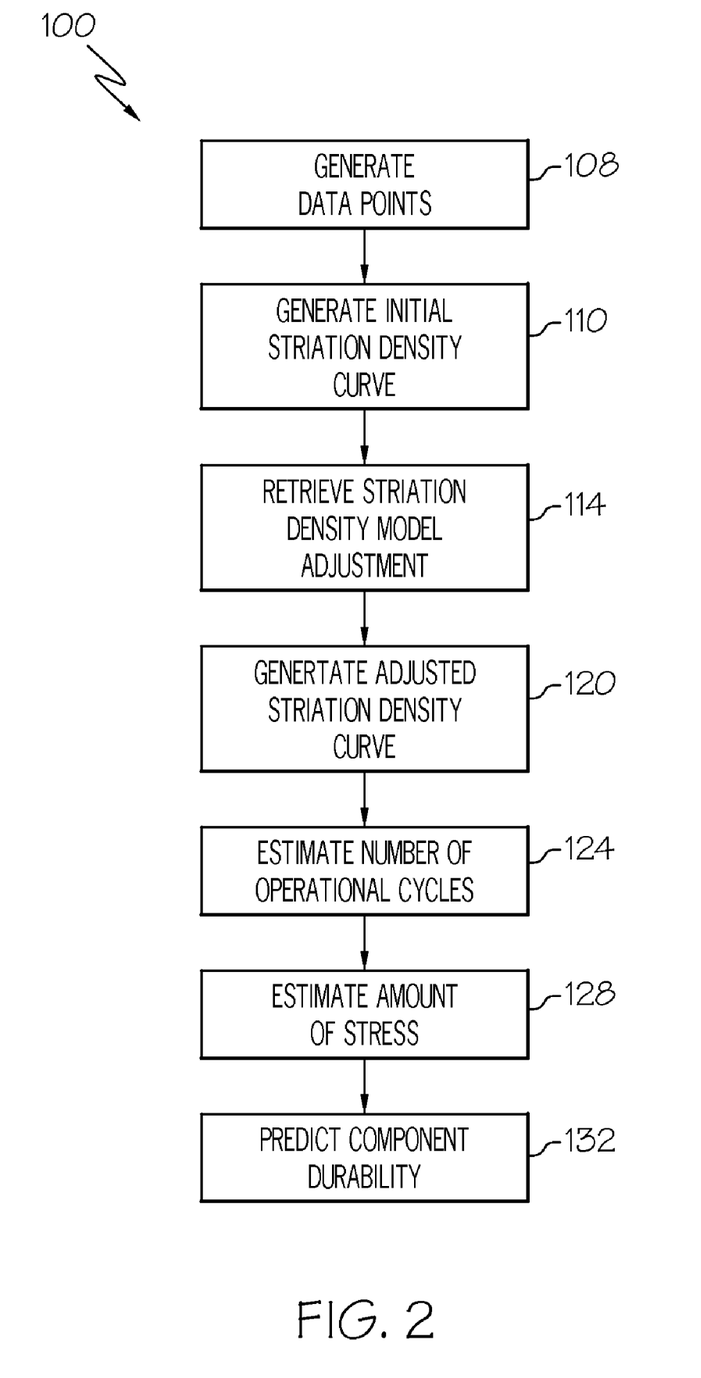
FIG. 2 is a flowchart of a process for performing striation density analysis for an engine component using a calibrated striation density model, in accordance with an exemplary embodiment of the present invention.

FIG. 2 is a flowchart of a striation density analysis process 100 for predicting durability of an engine component using a calibrated striation density model adjustment, in accordance with an exemplary embodiment of the present invention. The engine component comprises a material that has a fatigue-induced crack resulting from stress levels experienced over a plurality of operating cycles. In one preferred embodiment, a turbine blade, such as the turbine blade 10, is used as the engine component. In other embodiments, any one of a number of different components of a turbine engine, any one of various other different types of engines, and/or any one of a number of different types of devices and/or systems may be used for the component. As will be explained further below, the calibrated striation density model adjustment reflects a calibration at least in part based on the material.

As depicted in FIG. 2, the striation density analysis process 100 begins with the step of generating a plurality of data points (step 108). Each data point includes a striation density value and a crack depth value for a particular location along the crack of the engine component. In a preferred embodiment, each data point is generated by examining the engine component under a scanning electron microscope. Specifically, while the engine component is under the microscope, a crack depth is measured, and a value for a corresponding number of striations is calculated, at each of a plurality of locations along the crack. Preferably, a large number of data points are generated in this manner covering a large number of locations along the crack, to thereby provide a more accurate relationship between the striation density and the crack depth along the crack. For example, in one preferred embodiment, at least twenty different data points are generated in this manner, representing one data point for each of twenty or more locations along the crack. However, the number of data points may vary, for example depending on the embodiment, and/or depending on the type of engine component or crack therein.

An initial striation density curve is then generated using the data points (step 110). In a preferred embodiment, the initial striation density curve represents a first model comprising a first relationship between the striation density and the depth of the crack. The first relationship comprises an initial function mapping striation density versus crack depth. In one preferred embodiment, the initial function is generated as a relationship between the striation density and the crack depth for each of the data points, using a statistical regression model. Depending on the embodiment, various different types of regression models and/or various other different types of models and/or other techniques may be used.

The process continues by retrieving the above-referenced calibrated striation density model adjustment (step 114). The calibrated striation density model adjustment reflects a calibration of a striation density model at least in part based on the type of material. In addition, in a preferred embodiment, the calibrated striation density model adjustment reflects an additional calibration based on a temperature at which the engine component has been operating. Also in certain embodiments, the calibrated striation density model adjustment reflects one or more further calibrations based on a geometry of the engine component, a geometry of the crack therein, and/or one or more other factors. In a preferred embodiment, the calibrated striation density model adjustment is retrieved from a memory of a computer system, such as that described further below in connection with FIG. 5. An exemplary method for generating the calibrated striation density model adjustment is discussed further below in connection with a striation density model adjustment process of FIG. 3. It will be appreciated that steps 110 and 114, and/or various other steps of the striation density analysis process 100, may be performed concurrently or in a different order, regardless of the order presented in FIG. 2 and described herein in connection therewith.

The initial striation density curve is then adjusted by the calibrated striation density model adjustment to thereby generate an adjusted striation density curve (step 120). The adjusted striation density curve represents an adjusted model or relationship between the striation density and the depth of the crack, based at least in part on the striation density model adjustment. In one exemplary preferred embodiment, the initial striation density curve includes the initial function with a plurality of coefficients, and the calibrated striation density model adjustment includes a plurality of adjustment coefficients. In this preferred embodiment, coefficients in the initial striation density curve function are modified by the adjustment coefficients to thereby generate new, adjusted coefficients for a function for the adjusted striation density curve. In certain other exemplary embodiments, the calibrated striation density model adjustment comprises a set of adjustment points for different crack depths, and these adjustment points are used to modify respective points along the initial striation density curve. For example, in one such exemplary embodiment, the adjustment point for each particular crack depth may call for a percentage increase or decrease in the striation density of the initial striation density curve at such particular crack depth.

The adjusted striation density curve is then utilized to estimate a number of operational cycles for which the engine component has operated up until the crack reached a predetermined size, using fracture mechanics techniques known in the art (step 124). In addition, the adjusted striation density curve is also utilized to estimate an amount of stress that the engine component has experienced up until the crack reached a predetermined size, also using fracture mechanics techniques known in the art (step 128). Next, a measure of component durability is predicted, based on the number of operational cycles and the amount of stress (step 132). Preferably, the component durability refers to an expected lifespan for a device similar to the engine component. For example, in one preferred embodiment, the component durability refers to an estimated lifespan of a new engine component, having a similar structure and comprising the same material as the cracked engine component (but not having a crack) and operated under similar conditions, before such new engine component experiences a crack of a predetermined size.

Figure 3:
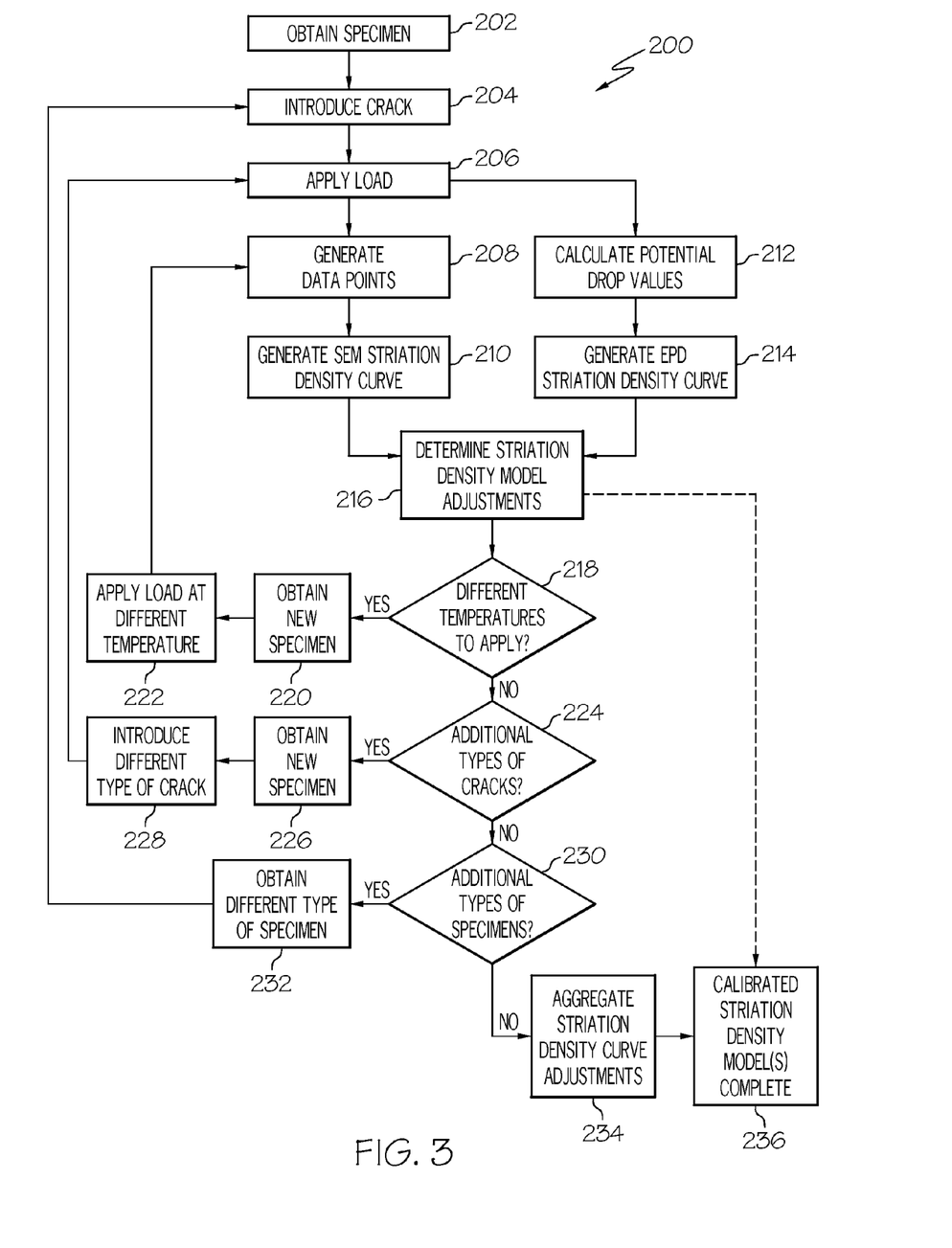
FIG. 3 is a flowchart of a process for generating a calibrated striation density model adjustment, such as that used in the process of FIG. 2, in accordance with an exemplary embodiment of the present invention.

FIG. 3 is a flowchart of a striation density model adjustment process 200 for generating a calibrated striation density model adjustment, such as the calibrated striation density model adjustment used in the striation density analysis process 100 of FIG. 2, in accordance with an exemplary embodiment of the present invention. As shown in FIG. 3, the striation density model adjustment process 200 begins with the step of obtaining a specimen (step 202). In a preferred embodiment, the specimen is chosen to be similar to engine components that are likely to be examined in the future using a striation density analysis process, for example, the above-referenced cracked engine component examined in connection with the striation density analysis process 100 discussed above in connection with FIG. 2.

Next, a crack is introduced in the specimen (step 204), and a load is applied to the specimen after introduction of the crack (step 206). The load causes the crack to propagate. Preferably, a known amount of load is applied to the specimen. In addition, the amount of load applied to the specimen is preferably similar to an amount of load typically experienced by one or more engine components that are likely to be examined in the future using a striation density analysis process, such as the striation density analysis process 100 discussed above in connection with FIG. 2. Furthermore, in a preferred embodiment, the load is introduced while the specimen is exposed to a predetermined temperature and/or other environmental conditions that are likely to be encountered during operation of such an engine component that is likely to be examined in the future using such a striation density analysis process. In addition, the crack introduced in the specimen preferably is of a type with a geometry that is likely to form in a similar engine component during operation over a number of operational cycles.

After the load is applied, a plurality of data points are generated (step 208). Somewhat similar to the data points of the striation density analysis process 100 of FIG. 2, each data point generated in step 208 includes a striation density value and a crack depth value for a particular location along the crack of the specimen. In a preferred embodiment, each data point is generated by examining the specimen under a scanning electron microscope. Specifically, while the specimen is under the microscope, a crack depth is measured and a value for a corresponding number of striations is calculated at each of a plurality of locations along the crack. Preferably, a large number of data points are generated in this manner covering a large number of locations along the crack, to thereby provide a more accurate relationship between the striation density and the crack depth along the crack. For example, in one preferred embodiment, at least twenty different data points are generated in this manner, representing one data point for each of twenty or more locations along the crack. However, the number of data points may vary, for example depending on the embodiment, and/or depending on the type of specimen or crack therein.

An SEM striation density curve is then generated using the data points obtained while the specimen is under the scanning electron microscope (SEM) (step 210). The SEM striation density curve represents a first model comprising a first relationship between the striation density and the depth of the crack. In a preferred embodiment, the SEM striation density curve represents an initial function mapping the striation density versus the crack depth along the various crack locations based on the data obtained using the SEM. Also in a preferred embodiment, the initial function is generated as a relationship between the crack depth and the corresponding striation density value for each of the data points, using a statistical regression model. Depending on the embodiment, various different types of regression models and/or various other different types of models and/or other techniques may be used.

In addition, electrical potential drop (EPD) values are calculated for the specimen at various points along the crack, using an electrical current (step 212). The EPD values are then used to generate an EPD striation density curve, using fracture mechanics techniques known in the art (step 214). The EPD striation density curve represents a second model comprising a second relationship between the striation density and the depth of the crack. In a preferred embodiment, the EPD striation density curve represents an additional function mapping striation density versus crack depth along the various crack locations, based on the calculated EPD values and known relationships between EPD and crack propagation, using fracture mechanics techniques known in the art. It will be appreciated that steps 208, 210 and steps 212, 214, and/or various other steps of the striation density model adjustment process 200, may be performed simultaneously or in a different order than that presented in FIG. 3 and described herein in connection therewith.

Next, a striation density model adjustment is determined (step 216). In a preferred embodiment, the SEM striation density curve includes the initial function with a plurality of coefficients, and the EPD striation density curve includes the additional function with a plurality of additional coefficients. In this preferred embodiment, the striation density model adjustment includes a plurality of adjustment coefficients representing a difference between the coefficients of the SEM striation density curve function and the coefficients of the EPD striation density curve function. The adjustment coefficients can then be stored in a memory of a computer system, such as that described further below in connection with FIG. 5, and can then be subsequently retrieved in step 114 of the striation density analysis process 100 of FIG. 2. Also in a preferred embodiment, the adjustment coefficients are intended to serve as adjustments to an initial striation density curve in step 120 of the striation density analysis process 100 of FIG. 2. As referenced above, in one such preferred embodiment, the adjustment coefficients reflect an addition or a subtraction to respective coefficients for such a subsequently-generated initial striation density curve in step 120 of the striation density analysis process 100 of FIG. 2.

Also as referenced above, in certain other exemplary embodiments, the striation density model adjustment comprises a set of adjustment points for different crack depths, which can be used to modify respective points along the initial striation density curve in step 120 of the striation density analysis process 100 of FIG. 2. For example, in one such exemplary embodiment, the adjustment point for each particular crack depth may call for a percentage increase or decrease in the striation density of the initial striation density curve at such particular crack depth in step 120 of the striation density analysis process 100 of FIG. 2. Additionally, the striation density model adjustment can comprise another type of adjustment mechanism, and/or can also be used as an adjustment for other curves, functions, and/or other types of models that may be used in performing various different types of striation density analysis techniques.

In certain embodiments, the calibrated striation density model is deemed to be complete (step 236) upon the determination of the striation density model adjustment. In certain other embodiments, various additional steps (namely, some or all of steps 218-234, described below) are performed to further calibrate the striation density model and/or to generate additional calibrated striation density models.

For example, in step 218, a determination is made as to whether there are any additional temperatures to apply during the application of the load. Such an additional temperature may include, for example, an additional temperature at which engine components are likely to operate. If there are additional temperatures to apply, then a new specimen is obtained (step 220), preferably with the same geometry as the original specimen obtained in step 202. Then, the known load is applied to the specimen at one of the additional temperatures (step 222), and steps 208-218 thereafter repeat until a determination is made in a subsequent iteration of step 218 that there are no additional temperatures to apply. Once a determination is made in an iteration of step 218 that there are no additional temperatures to apply, then the process proceeds to step 224 as described below.

In step 224, a determination is made as to whether there are any additional types of cracks to be implemented in a specimen. Such an additional type of crack may include another crack with a different geometry that is likely to be formed in an engine component over a number of operational cycles. If there are additional types of cracks to apply, then a new specimen is obtained (step 226), preferably with the same geometry as the original specimen obtained in step 202. Then, the new type of crack is introduced (step 228), and steps 206-224 thereafter repeat until a determination is made in a subsequent iteration of step 224 that there are no additional types of cracks to apply. Once a determination is made in an iteration of step 224 that there are no additional types of cracks to apply, then the process proceeds to step 230 as described below.

In step 230, a determination is made as to whether there are any additional types of specimens to test. Such an additional type of specimen may include a different geometry that is found in other engine components that are likely to be examined using striation density analysis. If there are additional types of specimens, then a new type of specimen is obtained (step 232) and steps 204-230 repeat until a determination is made in a subsequent iteration of step 230 that there are no additional types of specimens to test. Once a determination is made in an iteration of step 230 that there are no additional types of specimens to test, then the process proceeds to step 234 as described below.

The various striation density model adjustments from the various iterations of step 216 are then aggregated into one or more calibrated striation density models (step 234), at which point the one or more striation density adjustment models are deemed to be complete (step 236). In certain embodiments, some or all of steps 218-234, and/or other steps of the striation density model adjustment process 200, need not be completed to generate a desired calibrated striation density model. For example, in certain embodiments, a single calibrated striation density model may be generated for a particular type of material using a single specimen and testing the specimen using a single temperature and a single type of crack. In other embodiments, one or more calibrated striation density models may be generated for a particular type of material using multiple specimens, multiple temperatures, and/or multiple different types of cracks. Some of these embodiments may also use specimens with different geometries.

Accordingly, in some embodiments a plurality of different calibrated striation density models may be generated, each of which are calibrated based not only upon the material but also upon one or more additional factors such as the temperature, the geometry of the specimen, and/or the geometry of the crack. Likewise, multiple calibrated striation density models similarly can be generated such that each calibrated striation density model reflects a calibration based upon a different type of material, either alone or in combination with other factors such as those described above. As referenced above, the one or more calibrated striation density models are preferably stored, for example in a memory of a computer system such as that described further below in connection with FIG. 5, so that such calibrated striation density models can be subsequently accessed during the striation density analysis process 100 of FIG. 2.

Figure 4:
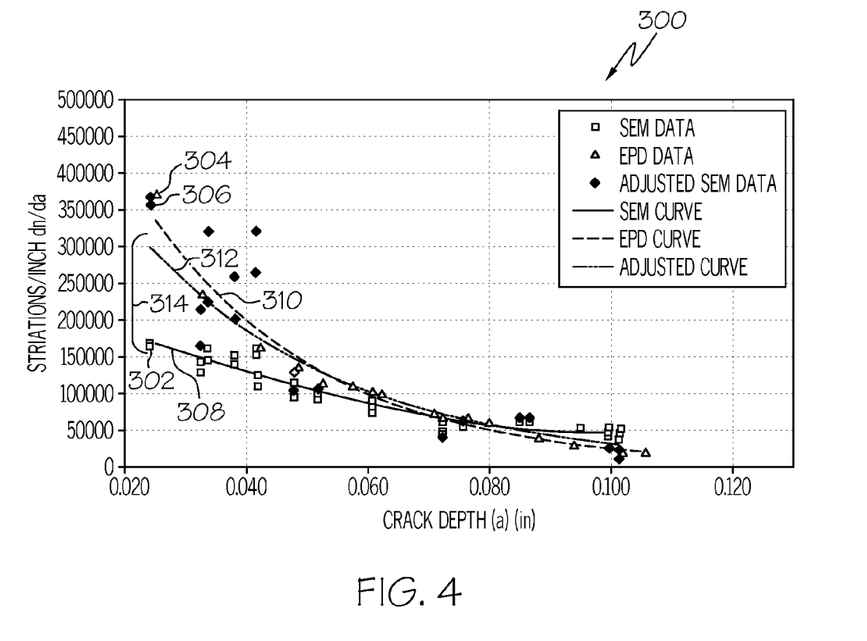
FIG. 4 is a graph showing a first striation density relationship, a second striation density relationship, and an adjustment to the first striation density relationship, for example that can be used as the calibrated striation density model in the process of FIG. 2 and/or that can be generated using the process of FIG. 3, in accordance with an exemplary embodiment of the present invention.

FIG. 4 is a graph 300 showing a first (SEM) striation density relationship reflecting SEM data, a second (EPD) striation density relationship reflecting EPD data, and an adjustment to the first (SEM) striation density relationship, for example that can be retrieved as the calibrated striation density model adjustment in step 114 of the striation density analysis process 100 of FIG. 2 and/or that can be generated using the striation density model adjustment process 200 of FIG. 3, in accordance with an exemplary embodiment of the present invention. Specifically, as depicted in FIG. 4, the graph 300 shows various SEM data points 302, EPD data points 304, and adjusted data points 306, as well as an SEM striation density curve 308, an EPD striation density curve 310, an adjusted striation density curve 312, and an adjustment 314 of an SEM data point 302 reflected in the adjusted striation density curve 312.

In a preferred embodiment, the SEM data points 302 are generated from analysis of a specimen under an SEM, for example as described above in connection with step 208 of the striation density model adjustment process 200 of FIG. 3. The EPD data points 304 are preferably generated from EPD calculations, for example as described above in connection with step 212 of the striation density model adjustment process 200 of FIG. 3. The SEM striation density curve 308 represents a relationship among the various SEM data points 302 (for example as generated in step 210 of the striation density model adjustment process 200 of FIG. 3), and the EPD striation density curve 310 represents a relationship among the various EPD data points 304 (for example as generated in step 214 of the striation density model adjustment process 200 of FIG. 3).

The adjusted data points 306 represent one or more adjustments 314 to the SEM data points 302 to make them consistent with the EPD data points 304. For example, in one preferred embodiment in accordance with step 216 of the striation density model adjustment process 200 of FIG. 3, each adjusted data point 306 represents the product of a variable scaling factor multiplied by the magnitude of the SEM striation density for a particular corresponding SEM data point 302. The result of this multiplication preferably very nearly equals the value of the EPD determined striation density for a corresponding particular EPD data point 304. Taken together, the adjusted data points 306 form the adjusted striation density curve 312. The adjustments 314 and/or the adjusted striation density curve 312 can be retrieved in step 114 of the striation density analysis process 100 of FIG. 2 and used, along with an initial striation density curve in accordance with step 120 of the striation density analysis process 100, to thereby generate the adjusted striation density curve referenced therein.

Figure 5:
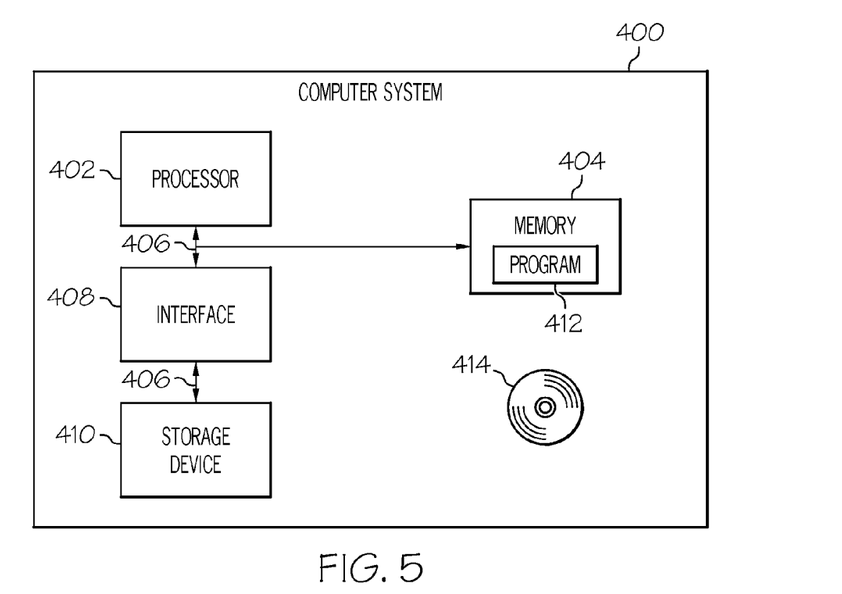
FIG. 5 is a functional block diagram of a computer system that can be used to implement the processes of FIG. 2 and/or FIG. 3, and/or to generate the first striation density relationship, the second striation density relationship, and the adjustment to the first striation density relationship of FIG. 4, in accordance with an exemplary embodiment of the present invention.

FIG. 5 is a functional block diagram of a computer system 400 that can be used to implement the striation density analysis process 100 process of FIG. 2 and/or the striation density model adjustment process 200 of FIG. 3, and/or to generate the SEM striation density curve 308, the EPD striation density curve 310, and the adjusted striation density curve 312 of FIG. 4, in accordance with an exemplary embodiment of the present invention. It will be appreciated that these processes and curves may also be generated, implemented, and/or utilized in connection with any one or more of a number of different types of computer systems and/or other systems and/or devices.

In the depicted embodiment, the computer system 400 includes a processor 402, a memory 404, a bus 406, an interface 408, and a storage device 410. The processor 402 performs the computation and control functions of the computer system 400, and may comprise any type of processor or multiple processors, single integrated circuits such as a microprocessor, or any suitable number of integrated circuit devices and/or circuit boards working in cooperation to accomplish the functions of a processing unit. During operation, the processor 402 executes one or more programs 412 preferably stored within the memory 404 and, as such, controls the general operation of the computer system 400.

In one embodiment, the memory 404 stores a program or programs 412 that executes one or more embodiments of the processes of the present invention, discussed in more detail below. The memory 404 can be any type of suitable memory. In addition, in a preferred embodiment, the memory 404 stores the one or more calibrated striation density models and the striation density model adjustments and coefficients contained therein, which may be generated in the striation density model adjustment process 200 of FIG. 3 and subsequently accessed in the striation density analysis process 100, and/or other processes, in various embodiments. The memory 404 may include one or more of various types of dynamic random access memory (DRAM) such as SDRAM, the various types of static RAM (SRAM), and the various types of non-volatile memory (PROM, EPROM, and flash). It should be understood that the memory 404 may be a single type of memory component, or it may be composed of many different types of memory components. In addition, the memory 404 and the processor 402 may be distributed across several different computers that collectively comprise the computer system 400. For example, a portion of the memory 404 may reside on a computer within a particular apparatus or process, and another portion may reside on a remote computer.

The bus 406 serves to transmit programs, data, status and other information or signals between the various components of the computer system 400. The bus 406 can be any suitable physical or logical means of connecting computer systems and components. This includes, but is not limited to, direct hard-wired connections, fiber optics, infrared and wireless bus technologies.

The interface 408 allows communication to the computer system 400, for example from a system driver and/or another computer system, and can be implemented using any suitable method and apparatus. It can include one or more network interfaces to communicate with other systems or components. The interface 408 may also include one or more network interfaces to communicate with technicians, and/or one or more storage interfaces to connect to storage apparatuses, such as the storage device 410.

The storage device 410 can be any suitable type of storage apparatus, including direct access storage devices such as hard disk drives, flash systems, floppy disk drives and optical disk drives. In one exemplary embodiment, the storage device 410 comprises a program product from which memory 404 can receive a program 412 that executes one or more embodiments of one or more processes of the present invention. As shown in FIG. 5, the storage device 410 can comprise a disk drive device that uses disks 414 to store data. As one exemplary implementation, the computer system 400 may also utilize an Internet website, for example for providing or maintaining data or performing operations thereon.

It will be appreciated that while this exemplary embodiment is described in the context of a fully functioning computer system, those skilled in the art will recognize that the mechanisms of the present invention are capable of being distributed as a program product in a variety of forms, and that the present invention applies equally regardless of the particular type of computer-readable signal bearing media used to carry out the distribution. Examples of signal bearing media include: recordable media such as floppy disks, hard drives, memory cards and optical disks (e.g., disk 414), and transmission media such as digital and analog communication links. It will similarly be appreciated that the computer system 400 may also otherwise differ from the embodiment depicted in FIG. 5, for example in that the computer system 400 may be coupled to or may otherwise utilize one or more remote computer systems and/or other control systems.

The processes and programs depicted in the Figures and described above are exemplary in nature, and may vary. Moreover, these processes and programs may be implemented or used in connection with any one or more of a number of different types of engines, vehicles, and/or various other devices, systems, processes, and/or environments. The processes and programs allow for the generation of a calibration for a striation density model with respect to a material, and for the performance of striation analysis using a calibrated striation density model, to thereby allow for more reliable, material-specific striation density analysis and improved and more reliable generation of data, estimates, and predictions based thereon.

While the invention has been described with reference to a preferred embodiment, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method for generating a calibration for a striation density model with respect to a material, the method comprising the steps of:
   generating a first relationship between a striation density and a depth of a crack in a specimen comprising the material via a processor;
   generating a second relationship between the striation density and the depth of the crack in the specimen via the processor; and
   calculating an adjustment to the striation density model using a comparison between the first relationship and the second relationship to generate the calibration for the striation density model based on the material via the processor for use in estimating operating conditions of an engine component.

2. The method of claim 1, wherein:
   the step of generating the first relationship comprises the steps of:
      counting a number of striations for each of a plurality of locations along the crack; and measuring a crack depth for each of the plurality of locations along the crack; and the step of generating the second relationship comprises the step of measuring a potential drop at each of the plurality of locations along the crack.

3. The method of claim 1, further comprising the steps of:
introducing the crack in the specimen; and
applying a load to the specimen;
wherein the steps of generating the first relationship, generating the second relationship, and calculating the adjustment occur after the load is applied to the specimen.

4. The method of claim 3, further comprising the steps of:
introducing a second crack in a second specimen;
applying a second load to the second specimen;
generating a first additional relationship between a striation density of the second crack and a depth of the second crack;
generating a second additional relationship between the striation density of the second crack and the depth of the second crack; and
calculating a second adjustment to the first additional relationship based on a comparison between the first additional relationship and the second additional relationship.

5. The method of claim 4, wherein:
the load is applied to the specimen at a first temperature;
the second load is applied to the second specimen at a second temperature; and
the first temperature and the second temperature are not equal to one another.

6. The method of claim 4, wherein the second specimen has a different geometry than the specimen.

7. The method of claim 4, wherein the second crack has a different geometry than the crack.

8. A method for performing striation analysis for a component of an engine, the component comprising a material, the method comprising the steps of:
generating a first relationship between a striation density and a depth of a crack in the component via a processor;
obtaining an adjustment based at least in part on the material via the processor; and
generating an adjusted relationship between the striation density and the depth of the crack in the component based at least in part on the first relationship and the adjustment via the processor for use in estimating operating conditions of the component of the engine.

9. The method of claim 8, wherein the adjustment is also based at least in part on a temperature to which the component has been exposed.

10. The method of claim 8, further comprising the step of:
estimating a level of stress experienced by the component based at least in part on the adjusted relationship.

11. The method of claim 10, further comprising the step of:
estimating a number of operational cycles for the component based at least in part on the adjusted relationship.

12. The method of claim 8, wherein the step of obtaining the adjustment comprises the steps of:
generating a first specimen relationship between a specimen striation density and a specimen depth of a specimen crack in a specimen comprising the material;
generating a second specimen relationship between the specimen striation density and the specimen depth of the specimen crack; and
calculating the adjustment based on a comparison between the first specimen relationship and the second specimen relationship.

13. The method of claim 12, wherein:
the step of generating the first specimen relationship comprises the steps of:
counting a number of striations for each of a plurality of locations along the specimen crack; and
measuring a specimen crack depth for each of the plurality of locations along the specimen crack; and
the step of generating the second specimen relationship comprises the step of measuring a potential drop at each of the plurality of locations along the specimen crack.

14. The method of claim 13, wherein the step of obtaining the adjustment further comprises the steps of:
introducing the specimen crack in the specimen; and
applying a load to the specimen;
wherein the steps of generating the first specimen relationship, generating the second specimen relationship, and calculating the adjustment occur after the load is applied to the specimen.

15. A method for generating a calibration for a striation density model with respect to a material, the method comprising the steps of:
introducing a crack in the specimen;
applying a load to the specimen;
generating a first relationship between a striation density and a depth of a crack in a specimen comprising the material after the first is applied to the specimen;
generating a second relationship between the striation density and the depth of the crack in the specimen after the load is applied to the specimen; and
calculating an adjustment to the striation density model using a comparison between the first relationship and the second relationship to generate the calibration for the striation density model based on the material.

16. The method of claim 15, wherein:
the step of generating the first relationship comprises the steps of:
counting a number of striations for each of a plurality of locations along the crack; and
measuring a crack depth for each of the plurality of locations along the crack; and
the step of generating the second relationship comprises the step of measuring a potential drop at each of the plurality of locations along the crack.

17. The method of claim 15, further comprising the steps of:
introducing a second crack in a second specimen;
applying a second load to the second specimen;
generating a first additional relationship between a striation density of the second crack and a depth of the second crack;
generating a second additional relationship between the striation density of the second crack and the depth of the second crack; and
calculating a second adjustment to the first additional relationship based on a comparison between the first additional relationship and the second additional relationship.

18. The method of claim 17, wherein:
the load is applied to the specimen at a first temperature;
the second load is applied to the second specimen at a second temperature; and
the first temperature and the second temperature are not equal to one another.

19. The method of claim 17, wherein the second specimen has a different geometry than the first specimen.

20. The method of claim 17, wherein the second specimen has a different geometry than the first specimen.

* * * * *